United States Patent
Rinsch et al.

(10) Patent No.: US 9,994,542 B2
(45) Date of Patent: Jun. 12, 2018

(54) PRODRUGS OF UROLITHINS AND USES THEREOF

(71) Applicant: AMAZENTIS SA, Lausanne (CH)

(72) Inventors: Christopher Lawrence Rinsch, Morges (CH); Rune Andreas Ringom, Uppsala (SE)

(73) Assignee: Amazentis SA (CH)

( * ) Notice: Subject to any disclaimer, the term of this patent is extended or adjusted under 35 U.S.C. 154(b) by 0 days. days.

(21) Appl. No.: 15/107,467

(22) PCT Filed: Dec. 23, 2014

(86) PCT No.: PCT/EP2014/079189
§ 371 (c)(1),
(2) Date: Jun. 23, 2016

(87) PCT Pub. No.: WO2015/097231
PCT Pub. Date: Jul. 2, 2015

(65) Prior Publication Data
US 2016/0332982 A1 Nov. 17, 2016

(30) Foreign Application Priority Data

Dec. 24, 2013 (GB) .................................. 1323008.1

(51) Int. Cl.
| | |
|---|---|
| A61K 31/352 | (2006.01) |
| A61K 31/4025 | (2006.01) |
| C07D 311/80 | (2006.01) |
| C07D 405/12 | (2006.01) |
| A61K 31/366 | (2006.01) |
| A61K 45/06 | (2006.01) |

(52) U.S. Cl.
CPC .......... *C07D 311/80* (2013.01); *A61K 31/366* (2013.01); *A61K 31/4025* (2013.01); *A61K 45/06* (2013.01); *C07D 405/12* (2013.01)

(58) Field of Classification Search
CPC .............. A61K 31/352; A61K 31/4025; C07D 311/80; C07D 405/12
USPC ................... 514/422, 455; 548/525; 549/280
See application file for complete search history.

(56) References Cited

U.S. PATENT DOCUMENTS

| | | |
|---|---|---|
| 2005/0282781 A1 | 12/2005 | Ghosal |
| 2007/0197567 A1 | 8/2007 | Sherris |

FOREIGN PATENT DOCUMENTS

| | | |
|---|---|---|
| WO | 2006007310 A2 | 1/2006 |
| WO | 2007127263 A2 | 11/2007 |
| WO | 2008016554 A1 | 2/2008 |

(Continued)

OTHER PUBLICATIONS

Islam et al., Biotransformation of 3-hydroxydibenzo-α-pyrone into 3,8 dihydroxydibenzo-α-pyrone and aminoacyl aonjugates by Aspergillus niger isolated from native "shilajit", Electronic Journal of Biotechnology, vol. 11, No. 3, Jul. 15, 2008, pp. 1-10.

(Continued)

*Primary Examiner* — Brenda L Coleman
(74) *Attorney, Agent, or Firm* — Foley Hoag LLP

(57) ABSTRACT

The invention provides compounds of formula (I) or salts thereof:

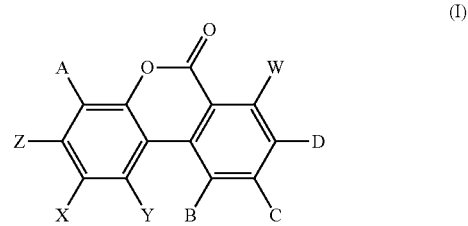

wherein:
A, B, C, D, W, X, Y and Z are as defined in the specification, and at least one of A, B, C, D, W, X, Y and Z is OR$^1$; each R$^1$ being independently H or C(=O)R$^2$, and at least one R$^1$ group being C(=O)R$^2$; where each R$^2$ is selected from:
CHR$^3$NHR$^4$, where R$^4$ is H and R$^3$ is a group selected from CH$_3$, CH$_2$CH(CH$_3$)$_2$, CH(CH$_3$)CH$_2$CH$_3$, CH$_2$Ph, CH$_2$-3-(1H-indole), CH$_2$CH$_2$SCH$_3$, CH$_2$OH, CHOHCH$_3$, CH$_2$SH, CH$_2$SeH and CH$_2$PhpOH,
wherein said R$^3$ group can optionally be substituted by one or more groups selected from halogen, cyano, nitro, OR$^4$ or C$_1$-C$_4$ alkyl;
or R$^3$ and R$^4$ together with the C and N atoms to which they are attached form a 5-membered heteroalkyl ring, wherein said heteroalkyl ring can optionally be substituted by one or more groups selected from halogen, cyano, nitro, OR$^4$ or C$_1$-C$_3$ alkyl,
wherein R$^4$ is C$_1$-C$_4$ alkyl optionally substituted with one or more halogen, cyano or nitro groups.

The compounds are effective pro-drugs for urolithins and they enable the ready delivery of urolithins to the site in the digestive tract where they can be absorbed into the body.

12 Claims, 3 Drawing Sheets

(56) References Cited

FOREIGN PATENT DOCUMENTS

WO   2012088519 A2   6/2012
WO   2014004902 A2   1/2014

OTHER PUBLICATIONS

Wilson et al., "Review on shilajit used in traditional Indian medicine", Journal of Ethnopharmacology, vol. 136, No. 1, 2011, pp. 1-9.
Heinrich et al., "Diet and healthy ageing 2100: Will we globalise local knowledge systems?", Ageing Research Reviews, vol. 7, No. 3, 2008, pp. 249-274.
International Search Report and Written Opinion issued in corresponding International Patent Application No. PCT/EP2014/079189 dated Mar. 9, 2015 (8 pages).

—— Example 1, pH 4, 0.77 mg/mL

—— Example 2, pH 4, 0.5 mg/mL first time

·········· Example 2, pH 4, 0.5 mg/mL second time

– – – Example 2, pH 4, 1.8 mg/mL

PRODRUGS OF UROLITHINS AND USES THEREOF

This application is a National Stage Application of PCT/EP2014/079189, filed Dec. 23, 2014, which claims priority to United Kingdom Patent Application No. 1323008.1, filed Dec. 24, 2013, which is incorporated in its entirety by reference herein.

The current invention relates to derivatives of urolithins and their use.

BACKGROUND

Urolithins are metabolites produced by the action of mammalian, including human, gut microbiota on ellagitannins and ellagic acid. Ellagitannins and ellagic acid are compounds commonly found in foods such as pomegranates, nuts and berries. Ellagitannins are minimally absorbed in the gut themselves. Urolithins are a class of compounds with the representative structures below and they have been shown to have potent effects on the improvement of a number of health conditions.

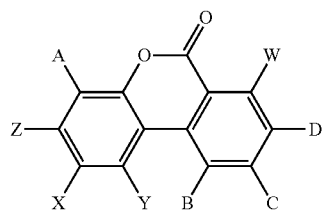

where A, B, C, D, W, X, Y and Z are each independently selected from H or OH, and at least one of them is OH.

In particular, the compounds Urolithin A and Urolithin B have been shown to be highly biologically active in vitro and in vivo.

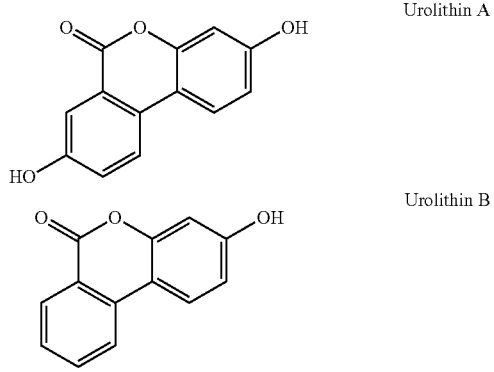

Urolithins have been proposed as treatments of a variety of conditions related to inadequate mitochondrial activity, including obesity, reduced metabolic rate, metabolic syndrome, diabetes mellitus, cardiovascular disease, hyperlipidemia, neurodegenerative diseases, cognitive disorder, mood disorder, stress, and anxiety disorder; for weight management, or to increase muscle performance or mental performance. See WO2012/088519 (Amazentis SA). In WO2007/127263 (The Regents of the University of California), the use of urolithins for the treatment of various neoplastic diseases is described.

International patent publication no. WO2014/004902 (derived from application PCT/US2013/48310) discloses a method of increasing autophagy, including specifically mitophagy, in a cell, comprising contacting a cell with an effective amount of a urolithin or a pharmaceutically acceptable salt thereof, thereby increasing autophagy, including specifically mitophagy, in the cell. Administration may be to a subject having a disease or condition selected from metabolic stress, cardiovascular disease, endothelial cell dysfunction, sarcopenia, muscle degenerative disease, Duchenne muscular dystrophy, alcoholic liver disease, nonalcoholic fatty liver disease, drug-induced liver injury, α1-antitrypsin deficiency, ischemia/reperfusion injury, inflammation, aging of the skin, inflammatory bowel disease, Crohn's disease, obesity, metabolic syndrome, type II diabetes mellitus, hyperlipidemia, osteoarthritis, neurodegenerative disease, Alzheimer's disease, Huntington's disease, Parkinson's disease, amyotrophic lateral sclerosis, age-related macular degeneration, mitochondrial diseases (including for example poor growth, loss of muscle coordination, muscle weakness, visual problems, hearing problems, heart disease, liver disease, kidney disease, gastrointestinal disorders, respiratory disorders, neurological problems, autonomic dysfunction sometimes learning disabilities, and dementia as a result of mitochondrial disease), muscle diseases; sporadic inclusion body myositis (sIBM), cancer, cognitive disorder, stress, and mood disorder.

Whilst urolithin compounds are known to possess properties that render them useful in a variety of therapies, they are highly water-insoluble. Consequently, formulation of urolithins into aqueous formulations is not straightforward. There thus remains a need for compositions of urolithins that are sufficiently soluble to allow for ready administration, to provide urolithin that is safe and active in the desired therapeutic use.

SUMMARY OF THE INVENTION

The invention provides compound of formula (I) or a salt thereof:

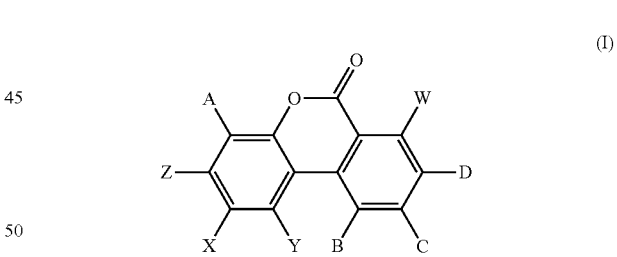

wherein:
A, B, C and D are each independently selected from H and $OR^1$,
W, X and Y are each independently selected from H and $OR^1$,
Z is selected from H and $OR^1$;
provided that at least one of A, B, C, D, W, X, Y and Z is $OR^1$;
each $R^1$ is independently H or $C(=O)R^2$, and at least one $R^1$ group is $C(=O)R^2$;
each $R^2$ is selected from:
$CHR^3NHR^4$, where $R^4$ is H and $R^3$ is a group selected from $CH_3$, $CH_2CH(CH_3)_2$, $CH(CH_3)CH_2CH_3$, $CH_2Ph$, $CH_2$-3-(1H-indole), $CH_2CH_2SCH_3$, $CH_2OH$, $CHOHCH_3$, $CH_2SH$, $CH_2SeH$ and $CH_2PhpOH$, wherein said $R^3$ group can optionally be substituted by one or more groups selected from halogen, cyano, nitro, $OR^A$ or $C_1$-$C_4$ alkyl;

or $R^3$ and $R^4$ together with the C and N atoms to which they are attached form a 5-membered heteroalkyl ring, wherein said heteroalkyl ring can optionally be substituted by one or more groups selected from halogen, cyano, nitro, $OR^A$ or $C_1$-$C_3$ alkyl, wherein $R^A$ is $C_1$-$C_4$ alkyl optionally substituted with one or more halogen, cyano or nitro groups.

The invention also provides a compound of formula (Ia) or a salt thereof for use as a medicament:

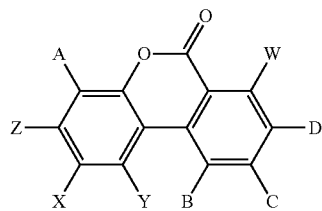

(Ia)

wherein:

A, B, C and D are each independently selected from H and $OR^1$,

W, X and Y are each independently selected from H and $OR^1$,

Z is selected from H and $OR^1$;

provided that at least one of A, B, C, D, W, X, Y and Z is $OR^1$;

each $R^1$ is independently H or C(=O)$R^2$, and at least one $R^1$ group is C(=O)$R^2$;

each $R^2$ is selected from:

$CHR^3NHR^4$ where $R^4$ is H and $R^3$ is a group selected from $CH_3$, $CH_2CH(CH_3)_2$, $CH(CH_3)CH_2CH_3$, $CH_2Ph$, $CH_2$-3-(1H-indole), $CH_2CH_2SCH_3$, $CH_2OH$, $CHOHCH_3$, $CH_2SH$, $CH_2SeH$ and $CH_2PhpOH$, wherein said $R^3$ group can optionally be substituted by one or more groups selected from halogen, cyano, nitro, $OR^A$ or $C_1$-$C_4$ alkyl, or $R^3$ and $R^4$ together with the C and N atoms to which they are attached form a 5-membered heteroalkyl ring, wherein said heteroalkyl ring can optionally be substituted by one or more groups selected from halogen, cyano, nitro, $OR^A$ or $C_1$-$C_3$ alkyl, wherein $R^A$ is $C_1$-$C_4$ alkyl, optionally substituted with one or more halogen, cyano or nitro groups.

The invention further provides a compound of formula (Ia) or a salt thereof for use as a medicament wherein W, X and Y are H, A, B and C are H, and D and Z are both $OR^1$, and each $R^1$ is independently H or C(=O)$R^2$, and at least one $R^1$ group is C(=O)$R^2$;

each $R^2$ is selected from:

$CHR^3NHR^4$ where $R^4$ is H and $R^3$ is selected from H or a group selected from $CH_3$, $CH_2CH(CH_3)_2$, $CH(CH_3)CH_2CH_3$, $CH_2Ph$, $CH_2$-3-(1H-indole), $CH_2CH_2SCH_3$, $CH_2OH$, $CHOHCH_3$, $CH_2SH$, $CH_2SeH$ and $CH_2PhpOH$, wherein said $R^3$ group can optionally be substituted by one or more groups selected from halogen, cyano, nitro, $OR^A$ or $C_1$-$C_4$ alkyl, or $R^3$ and $R^4$ together with the C and N atoms to which they are attached form a 5-membered heteroalkyl ring, wherein said heteroalkyl ring can optionally be substituted by one or more groups selected from halogen, cyano, nitro, $OR^A$ or $C_1$-$C_3$ alkyl, wherein $R^A$ is $C_1$-$C_4$ alkyl, optionally substituted with one or more halogen, cyano or nitro groups.

The compounds of the invention are more water soluble than the underivatised urolithins. The current inventors have demonstrated that, under relevant conditions, including when orally administered, they are hydrolysed to release the urolithin portion of the compound, which is bioavailable. The compounds are thus effective pro-drugs for urolithins and they enable the ready delivery of urolithins to the site in the digestive tract where they can be absorbed into the body. The compounds are sufficiently stable to enable delivery, but they are sufficiently susceptible to hydrolysis to enable delivery of the urolithin portion to the bloodstream before the compound is excreted from the body.

The invention therefore further provides compounds of formula (I) or (Ia) or salts thereof for use in the treatment of a disease or condition selected from the group consisting of metabolic syndrome, reduced metabolic rate, metabolic stress, cardiovascular disease, endothelial cell dysfunction, sarcopenia, muscle degenerative disease, Duchenne muscular dystrophy, alcoholic liver disease, non-alcoholic fatty liver disease (NAFLD), Nonalcoholic steatohepatitis (NASH), drug-induced liver injury, drug-induced cravings, anaemia disorders, α1-antitrypsin deficiency, ischemia/reperfusion injury, aging of the skin, inflammatory bowel disease, Crohn's disease, obesity, metabolic syndrome, type II diabetes mellitus, hyperlipidemia, osteoarthritis, neurodegenerative disease, Alzheimer's disease, Parkinson's disease, Huntington's disease, anxiety disorder, ulceration, amyotrophic lateral sclerosis, age-related macular degeneration, mitochondrial diseases (including for example poor growth, loss of muscle coordination, muscle weakness, visual problems, hearing problems, heart disease, liver disease, kidney disease, gastrointestinal disorders, respiratory disorders, neurological problems, autonomic dysfunction sometimes learning disabilities, and dementia as a result of mitochondrial disease. Further diseases related to mitochondrial dysfunction include: Diabetes mellitus and deafness (DAD); Leber's hereditary optic neuropathy (LHON); Leigh syndrome (subacute sclerosing encephalopathy); neuropathy, ataxia, retinitis pigmentosa, and ptosis (NARP); myoneurogenic gastrointestinal encephalopathy (MNGIE); Myoclonic Epilepsy with Ragged Red Fibers (MERRF); Mitochondrial myopathy, encephalomyopathy, lactic acidosis, stroke-like symptoms (MELAS); and mtDNA depletion), sporadic inclusion body myositis (sIBM), cancer, cognitive disorder, stress, and mood disorder; for improving cognitive function; for weight management; or to increase muscle or mental performance. The compounds of formula (I) or (Ia) or salts thereof are particularly suitable for use in improving muscle function, muscle strength, muscle endurance and muscle recovery.

In particular, the invention therefore further provides compounds of formula (I) or (Ia) or salts thereof for use in the treatment of a disease or condition selected from the group consisting of metabolic syndrome, reduced metabolic rate, metabolic stress, cardiovascular disease, endothelial cell dysfunction, sarcopenia, muscle degenerative disease, Duchenne muscular dystrophy, alcoholic liver disease, non-alcoholic fatty liver disease, drug-induced liver injury, drug-induced cravings, anaemia disorders, α1-antitrypsin deficiency, ischemia/reperfusion injury, inflammation, aging of the skin, inflammatory bowel disease, Crohn's disease, obesity, metabolic syndrome, type II diabetes mellitus, hyperlipidemia, osteoarthritis, neurodegenerative disease, Alzheimer's disease, Parkinson's disease, anxiety disorder, ulceration, amyotrophic lateral sclerosis, age-related macular degeneration, cancer, cognitive disorder, stress, and mood disorder; for improving cognitive function; for weight management; or to increase muscle or mental performance.

The invention further provides compounds of formula (I) or (Ia) or a salt thereof for use in the treatment of a disease or condition selected from the group consisting of metabolic stress, sarcopenia, muscle degenerative disease, Duchenne muscular dystrophy, alcoholic liver disease, nonalcoholic fatty liver disease, drug-induced liver injury, α1-antitrypsin deficiency, ischemia/reperfusion injury, inflammatory bowel disease, Crohn's disease, Alzheimer's disease, Parkinson's disease, amyotrophic lateral sclerosis, and cancer.

The invention further provides compounds of the formula (I) or (Ia) or salts thereof for increasing autophagy or mitophagy in a cell.

The compounds of formula (I) or (Ia) may exist in the form of salts, and such salts form part of this invention. Further, the compounds may exist in the form of solvates, for example hydrates, and solvates should also be understood to fall within the scope of this invention.

DETAILED DESCRIPTION OF THE INVENTION

Figure 1:
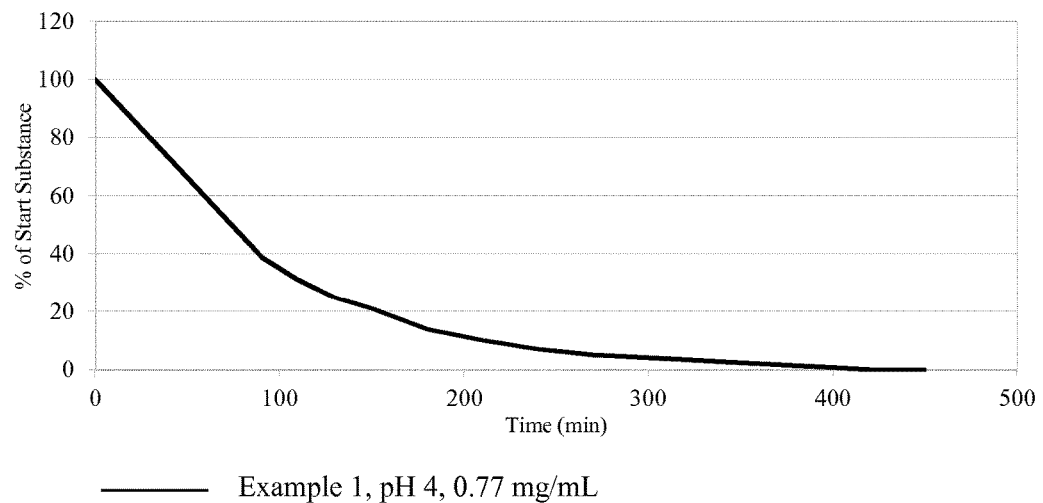
FIG. 1 shows the stability of the compound of Example 1 in solution over time.

The compounds of the invention include at least one ester group —OC(=O)$R^2$. On administration, the ester group is hydrolysed in the body to urolithin and $R^2$C(=O)OH. The urolithin can then exert its biological effect.

Particularly suitable compounds are compounds in which the various substituents are such that the core part of the compound is a naturally-occuring urolithin. Thus, Z is preferably $OR^1$. W, X and Y are preferably all H. Particularly suitable compounds are compounds in which A, B, C and D are such that the core part of the compound is urolithin A or urolithin B. That is to say that W, X and Y are preferably all H, the Z is preferably $OR^1$, and that A, B and C are preferably all H. If A, B and C are all H, D is H and Z is $OR^1$, then the core part of the compound is Urolithin B. If A, B and C are all H, and D and Z are both $OR^1$, then the core part of the compound is Urolithin A.

In a Urolithin A compound, both D and Z are $OR^1$. At least one of the $R^1$ groups is C(=O)$R^2$. In one embodiment, one $R^1$ group is H and the other is C(=O)$R^2$; in another embodiment, both $R^1$ groups are C(=O)$R^2$. In that case the two $R^2$ groups may be the same or different. It is convenient for them to be the same.

As $R^2$ is CHR$^3$NHR$^4$, $R^2$C(=O)OH is an amino acid. This is preferably a naturally occurring amino acid. Preferably such groups have the stereochemistry of a naturally occurring amino acid. That is to say that they are L-amino acids. For most amino acids this equates to the (S) isomer. For cysteine, the higher ranking of sulphur means that the configuration is termed (R). When $R^4$ is H and $R^3$ is CH$_3$, the released amino acid is alanine. Pairs of $R^4$ and $R^3$ groups give rise to particular amino acids as set out in Table 1.

TABLE 1

| | | released amino acids | |
|---|---|---|---|
| $R^4$ | $R^3$ | released amino acid | Amino acid structure |
| H | CH$_3$ | Alanine | 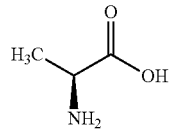 |
| H | CH$_2$CH(CH$_3$)$_2$ | Leucine | 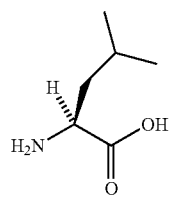 |
| H | CH(CH$_3$)CH$_2$CH$_3$ | Isoleucine | 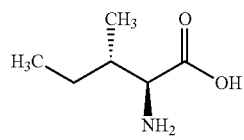 |

TABLE 1-continued released amino acids

| $R^4$ | $R^3$ | released amino acid | Amino acid structure |
|---|---|---|---|
| H | CH$_2$Ph | Phenylalanine | (structure of L-phenylalanine) |
| H | CH$_2$-3-(1H-indole) | Tryptophan | (structure of L-tryptophan) |
| H | CH$_2$CH$_2$SCH$_3$ | Methionine | (structure of L-methionine) |
| H | CHOHCH$_3$ | Threonine | (structure of L-threonine) |
| H | CH$_2$OH | Serine | (structure of L-serine) |
| H | CH$_2$SH | Cysteine | (structure of L-cysteine) |
| H | CH$_2$SeH | Selenocysteine | (structure of L-selenocysteine) |
| H | CH$_2$PhpOH | Tyrosine | (structure of L-tyrosine) |
| $R^3$ and $R^4$ together with the C and N atoms to which they are attached form a 2-pyrrolidine ring | | Proline | (structure of L-proline) (S) |

Preferably, $R^2$ is $CHR^3NHR^4$, where $R^4$ is H and $R^3$ is selected from $CH_3$, $CH_2CH(CH_3)_2$, $CH(CH_3)CH_2CH_3$, $CH_2Ph$, $CH_2$-3-(1H-indole), $CH_2CH_2SCH_3$, $CH_2OH$, $CHOHCH_3$, $CH_2SH$, $CH_2SeH$ or $CH_2PhpOH$, or $R^3$ and $R^4$ together with the C and N atoms to which they are attached form an unsubstituted 5-membered heteroalkyl ring. Compounds in which $R^2$ is $CHR^3NHR^4$ where $R^4$ is H and $R^3$ is selected from $CH_3$, $CH_2CH(CH_3)_2$ or $CH(CH_3)CH_2CH_3$, or in which $R^3$ and $R^4$ together with the C and N atoms to which they are attached form an unsubstituted 5-membered heteroalkyl ring have particularly advantageous solubility and stability properties and they are particularly preferred.

The following compounds in Table 2 can specifically be mentioned.

TABLE 2

| Compound | Structure | Shorthand name |
|---|---|---|
| 2 | 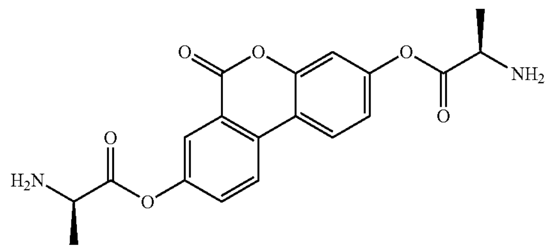 [SMILES: C[C@@H](N)C(=O)Oc1ccc2c(c1)oc(=O)c1cc(OC(=O)[C@@H](C)N)ccc12] | Di-alanine - Urolithin A |
| 4 | 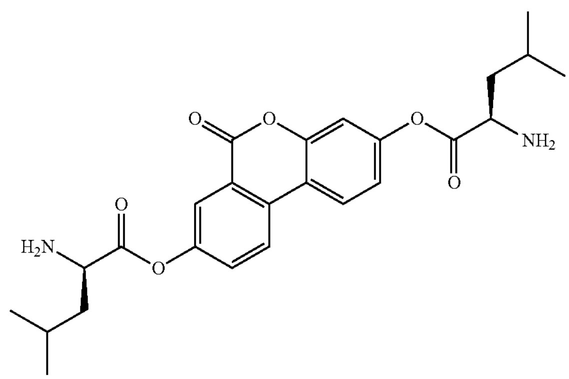 [SMILES: CC(C)C[C@@H](N)C(=O)Oc1ccc2c(c1)oc(=O)c1cc(OC(=O)[C@H](N)CC(C)C)ccc12] | Di-leucine - Urolithin A |
| 5 | 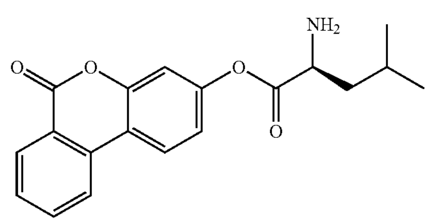 [SMILES: CC(C)C[C@H](N)C(=O)Oc1ccc2c(c1)oc(=O)c1ccccc12] | Leucine - Urolithin B |
| 6 | 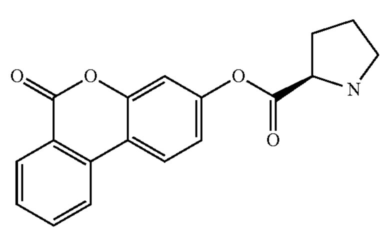 [SMILES: O=C(Oc1ccc2c(c1)oc(=O)c1ccccc12)[C@H]1CCCN1] | Proline - Urolithin B |

The following compounds in Table 3 may also specifically be mentioned.

TABLE 3

| Compound | Structure | Shorthand name |
|---|---|---|
| 1 | 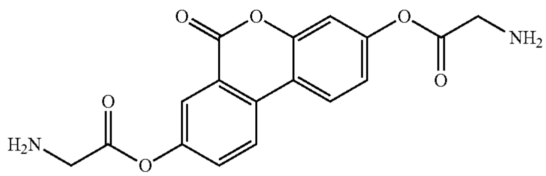 [SMILES: NCC(=O)Oc1ccc2c(c1)oc(=O)c1cc(OC(=O)CN)ccc12] | Di-glycine - Urolithin A |
| 3 | 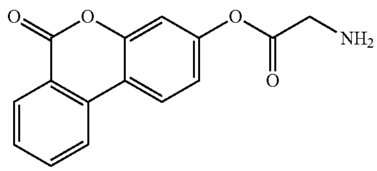 [SMILES: NCC(=O)Oc1ccc2c(c1)oc(=O)c1ccccc12] | Glycine - Urolithin B |

When the urolithin is released following administration, it can exert its biological effects in the body. The $R^2C(=O)OH$ acid is also released. It is an important aspect of the present invention that the $R^2$ groups are chosen such that the $R^2C(=O)OH$ released is a product with no detrimental effect on the subject, that is to say, the $R^2C(=O)OH$ should have either no biological effect, or only beneficial effects. Preferably $R^2C(=O)OH$ is a compound that is of natural origins and generally regarded as safe under the GRAS provisions issued by the US Food and Drug Administration.

Formulations and Administrations

The compounds of formula (I) or (Ia) or salts thereof may be administered to a subject alone or together with at least one other active agent or carrier, in any of a variety of ways. For example, they may be administered orally or parenterally. The subject may be a mammal (including a companion animal), especially a human. The compounds may be formulated as pharmaceutical compositions, or they may be formulated as foods (including drinks) or dietary supplements. They may also be formulated as powders that are admixed with a food or beverage immediately before administration or consumption.

As such, the compound can be administered in any of a variety of suitable forms, including neat compound, natural foods, processed foods, natural juices, concentrates and extracts. Tablets, capsules, powders, granules, injectable solutions, microcapsules, nano-capsules, liposomes, plasters, inhalation forms, nose sprays, nosedrops, eyedrops, sublingual tablets, and sustained-release preparations, may all be used.

Preferably, oral administration is used, whether as a pharmaceutical formulation or as a food or dietary supplement. Pharmaceutical dosage forms for oral administration include solid, semi-solid, or liquid forms, such as tablets, capsules, powders, granules, solutions, or suspensions. Alternative dosage forms for alternative administration methods include suppositories, injectable solutions, inhalants, gels, creams, microspheres, implants, and aerosols.

In one preferred embodiment, the compounds of the invention are formulated as foods or dietary supplements, including food additives, food ingredients, functional foods, medical foods, nutraceuticals, or food supplements. In certain embodiments, compounds of the invention can be included in nutraceutical or functional beverages of varying volumes to permit the administration of a daily dose in a convenient format. Beverages may include products formulated as gels. As a non-limiting example, beverages may deliver effective doses in a final volume ranging from 5 mL to 1,000 mL, delivered as a single dose or multiple doses.

Compounds of the invention may also be formulated as veterinary products, or as functional foods or beverages, for administration to animals.

The compounds of formula (I) or (Ia) may be in the form of a salt. This may be a pharmaceutically acceptable salt. Suitable salts may for example be derived from an acid selected from acetic, adipic, benzenesulfonic, benzoic, camphorsulfonic, citric, ethanesulfonic, fumaric, gluconic, glutamic, glycolic, hydrobromic, hydrochloric, lactic, maleic, malic, mandelic, methanesulfonic, mucic, nitric, oxalic, pantothenic, phosphoric, succinic, sulfuric, tartaric, p-toluenesulfonic, xinafoic (1-hydroxy-2-naphthoic acid), naphthalene-1,5-disulfonic acid and the like. Hydrochloride salts are especially convenient.

The compounds may also be used in appropriate association with other pharmaceutically active compounds, or with other food additives. Other pharmaceutically active compounds which may be co-administered or co-formulated with the compounds of the present invention include rapamycin, resveratrol, metformin, and spermidine.

The compounds may in particular be used in association with an agent that is useful in the treatment of health conditions involving a mitochondrial disorder. Such agents include compounds coenzyme Q10 (CoQ10) as ubiquinol, CoQ10 as ubiquinone, riboflavin (vitamin B2), L-creatine, L-arginine, L-carnitine, B50 or B100 (B vitamin complexes), vitamin E, vitamin C, alpha-lipoic acid, and folinic acid (e.g., as leucovorin). Thus the invention provides a combination of a compound of the invention with one or more compounds selected from the agents in the previous sentence.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into liquid preparations by dissolving, suspending or emulsifying them in an aqueous or nonaqueous solvent, such as vegetable or other similar oils, synthetic aliphatic acid glycerides, esters of higher aliphatic acids or propylene glycol; and if desired with conventional additives such as solubilizers, isotonic agents, suspending agents, emulsifying agents, stabilizers and preservatives. The compounds can be utilized in aerosol formulation to be administered via inhalation. They can be made into suppositories by mixing with a variety of bases such as emulsifying bases or water-soluble bases.

Unit dosage forms for oral administration such as syrups, elixirs, and suspensions may be provided wherein each dosage unit, for example, teaspoonful, tablespoonful, tablet or capsule, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier, wherein each dosage unit, for example, mL or L, contains a predetermined amount of the composition containing one or more compounds of the present invention.

In one embodiment, the compounds are provided as a dietary supplement which is provided as a solid, for example as a powder or granules, or liquid suitable for adding by the consumer to a food or beverage. For example, the dietary supplement may be in the form of a powder or granules, to be used by mixing into a beverage, or by stirring into a semi-solid food such as a pudding, topping, sauce, puree, cooked cereal, or salad dressing, for instance, or by otherwise adding to a food or drink. It may for example be enclosed in a compartment of the packaging and be designed to mix with the food or beverage upon opening just prior to consumption. For example, the compound may be placed in the cap of a water (or other liquid) bottle and released into the beverage upon turning the cap. The compound then dissolves in the beverage just prior to consumption. As such, the compound could be placed in the cap of a food or beverage container for release immediately before consumption, or it may be provided as a separate unit within the packaging of food or drink. The compound may be provided in a kit together with a food or beverage container.

Dietary supplements may comprise one or more inert ingredients, especially if it is desirable to limit the number of calories added to the diet by the dietary supplement. For example, a dietary supplement may also contain optional ingredients including, for example, herbs, vitamins, minerals, preservatives, enhancers, colorants, sweeteners, flavourants, inert ingredients, and the like. In some embodiments, dietary supplements further comprise vitamins and minerals including, but not limited to, calcium phosphate or acetate, tribasic; potassium phosphate, dibasic; magnesium; magnesium salts, for example magnesium sulfate or oxide; salt (sodium chloride); potassium chloride or acetate; ascorbic acid; ferric orthophosphate; niacin, niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D; vitamin D3; vitamin E; vitamin B; cyanocobalamin; sodium selenite; copper sulfate; vitamin A; vitamin C; inositol; potassium iodide; L-tryptophan; nicotinic acid; nicotinamide; omega-3 fatty acid (such as DHA, EPA and ALA); anthocyanines; isoflavones; choline; UMP; soy phospholipids; phosphatidyl serine; S-adenosyl-methionine (SAM); acetyl-L-carnitine (ALCAR); magnesium salts; magnesium acetate; magnesium chloride; magnesium citrate; magnesium lactate; magnesium gluconante; and magnesium pidolate. Thus the invention provides a combination of a compound of the invention with one or more compounds selected from the agents in the previous sentence.

Solutions or suspensions containing compounds of the invention optionally comprise one or more flavourings. Flavourings may assist in making the solutions in their diluted form for ingestion more palatable. The optimal level of flavouring depends on the intensity of flavour desired, and the nature and strength of the flavour in question. Sweeteners may also be present. Typical sweeteners include sugar, aspartame, acesulfame potassium (acesulfame K), sucralose and saccharine and combinations thereof. Preservatives may also be added to the formulations to extend product shelf life. Various preservatives are known for use in liquid oral preparations. Examples of such preservatives include calcium disodium EDTA, sodium propyl paraben, methyl paraben, ethyl paraben, propyl paraben, benzyl alcohol and phenoxyethanol. Further preservatives that are known for use in liquid oral preparations (including foods) include benzoic acid, dehydroacetic acid, sorbic acid, Bronopol, propylene glycol and glyceryl triacetate. Alcohols are used as preservatives in some preparations.

If desired, the composition may contain an effervescent, that is, an agent comprising one or more compounds which, act individually or together, evolve a gas on contact with water. The gas evolved is generally oxygen or, most commonly, carbon dioxide.

Treatments Using Compounds of the Invention

As mentioned above, the invention provides compounds of formula (I) or (Ia) or salts thereof for use in the treatment of a disease or condition selected from the group consisting of metabolic syndrome, reduced metabolic rate, metabolic stress, cardiovascular disease, sarcopenia, muscle degenerative disease, Duchenne muscular dystrophy, alcoholic liver disease, nonalcoholic fatty liver disease (NAFLD), Nonalcoholic steatohepatitis (NASH), drug-induced liver injury, drug-induced cravings, anaemia disorders, α1-antitrypsin deficiency, ischemia/reperfusion injury, inflammation, inflammatory bowel disease, Crohn's disease, obesity, metabolic syndrome, type II diabetes mellitus, hyperlipidemia, osteoarthritis, neurodegenerative disease, Alzheimer's disease, Parkinson's disease, Huntington's disease, anxiety disorder, ulceration, amyotrophic lateral sclerosis, mitochondrial diseases (including for example poor growth, loss of muscle coordination, muscle weakness, visual problems, hearing problems, heart disease, liver disease, kidney disease, gastrointestinal disorders, respiratory disorders, neurological problems, autonomic dysfunction sometimes learning disabilities, and dementia as a result of mitochondrial disease. Further diseases related to mitochondrial dysfunction include: Diabetes mellitus and deafness (DAD); Leber's hereditary optic neuropathy (LHON); Leigh syndrome (subacute sclerosing encephalopathy); neuropathy, ataxia, retinitis pigmentosa, and ptosis (NARP); myoneurogenic gastrointestinal encephalopathy (MNGIE); Myoclonic Epilepsy with Ragged Red Fibers (MERRF); Mitochondrial myopathy, encephalomyopathy, lactic acidosis, stroke-like symptoms (MELAS); and mtDNA depletion), sporadic inclusion body myositis (sIBM), and cancer, cognitive disorder, stress, and mood disorder; for improving cognitive function; for weight management; or to increase muscle or mental performance. The compounds of formula (I) or (Ia)

or salts thereof are particularly suitable for use in improving muscle function, muscle strength endurance and muscle recovery.

In particular, the invention provides compounds of formula (I) or (Ia) or salts thereof for use in the treatment of a disease or condition selected from the group consisting of metabolic syndrome, reduced metabolic rate, metabolic stress, cardiovascular disease, sarcopenia, muscle degenerative disease, Duchenne muscular dystrophy, alcoholic liver disease, nonalcoholic fatty liver disease, drug-induced liver injury, drug-induced cravings, anaemia disorders, α1-antitrypsin deficiency, ischemia/reperfusion injury, inflammation, inflammatory bowel disease, Crohn's disease, obesity, metabolic syndrome, type II diabetes mellitus, hyperlipidemia, osteoarthritis, neurodegenerative disease, Alzheimer's disease, Parkinson's disease, anxiety disorder, ulceration, amyotrophic lateral sclerosis, and cancer, cognitive disorder, stress, and mood disorder; for improving cognitive function; for weight management; or to increase muscle or mental performance.

The invention further provides compounds of formula (I) or (Ia) or a salt thereof for use in the treatment of a disease or condition selected from the group consisting of metabolic stress, sarcopenia, muscle degenerative disease, Duchenne muscular dystrophy, alcoholic liver disease, nonalcoholic fatty liver disease, drug-induced liver injury, α1-antitrypsin deficiency, ischemia/reperfusion injury, inflammatory bowel disease, Crohn's disease, Alzheimer's disease, Parkinson's disease, amyotrophic lateral sclerosis, and cancer.

The invention further provides compounds of the formula (I) or (Ia) or salts thereof for increasing autophagy or mitophagy in a cell. For example, the autophagy or mitophagy may be in embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, epidermal (i.e. skin) cells (including keratinocytes and fibroblasts), kidney cells, and germ cells. It may thus for example treat or prevent a disease or condition selected from the group consisting of metabolic syndrome, reduced metabolic rate, metabolic stress, cardiovascular disease, sarcopenia, muscle degenerative disease, Duchenne muscular dystrophy, alcoholic liver disease, nonalcoholic fatty liver disease, drug-induced liver injury, drug-induced cravings, anaemia disorders, α1-antitrypsin deficiency, ischemia/reperfusion injury, inflammation, inflammatory bowel disease, Crohn's disease, obesity, metabolic syndrome, type II diabetes mellitus, hyperlipidemia, osteoarthritis, neurodegenerative disease, Alzheimer's disease, Parkinson's disease, anxiety disorder, ulceration, amyotrophic lateral sclerosis, and cancer, cognitive disorder, stress, and mood disorder; or it can assist with weight management, or increase muscle or mental performance.

Amongst the neurodegenerative diseases, there may specifically be mentioned AIDS dementia complex, Alzheimer's disease, amyotrophic lateral sclerosis, adrenoleukodystrophy, Alexander disease, Alper's disease, ataxia telangiectasia, Batten disease, bovine spongiform encephalopathy (BSE), Canavan disease, corticobasal degeneration, Creutzfeldt-Jakob disease, dementia with Lewy bodies, fatal familial insomnia, frontotemporal lobar degeneration, Huntington's disease, Kennedy's disease, Krabbe disease, Lyme disease, Machado-Joseph disease, multiple sclerosis, multiple system atrophy, neuroacanthocytosis, Niemann-Pick disease, Parkinson's disease, Pick's disease, primary lateral sclerosis, progressive supranuclear palsy, Refsum disease, Sandhoff disease, diffuse myelinoclastic sclerosis, spinocerebellar ataxia, subacute combined degeneration of spinal cord, tabes dorsalis, Tay-Sachs disease, toxic encephalopathy, transmissible spongiform encephalopathy, and wobbly hedgehog syndrome. In one embodiment, the neurodegenerative disease is selected from the group consisting of Alzheimer's disease, amyotrophic lateral sclerosis, Huntington's disease, and Parkinson's disease. In one embodiment, the neurodegenerative disease is Alzheimer's disease.

An aspect of the invention is in improving cognitive function. In one embodiment, the cognitive function is selected from the group consisting of perception, memory, attention, speech comprehension, speech generation, reading comprehension, creation of imagery, learning, and reasoning. In one embodiment, the cognitive function is selected from the group consisting of perception, memory, attention, and reasoning. In one embodiment, the cognitive function is memory.

An aspect of the invention is in the treatment of cognitive disorder. In one embodiment, the cognitive disorder is selected from the group consisting of delirium, dementia, learning disorder, attention deficit disorder (ADD), and attention deficit hyperactivity disorder (ADHD). In one embodiment, the cognitive disorder is a learning disorder. In one embodiment, the cognitive disorder is attention deficit disorder (ADD). In one embodiment, the cognitive disorder is attention deficit hyperactivity disorder (ADHD).

An aspect of the invention is in the treatment of stress-induced or stress-related cognitive deficit. An aspect of the invention is in the treatment of a mood disorder. In one embodiment, the mood disorder is selected from the group consisting of depression, postpartum depression, dysthymia, and bipolar disorder. In one embodiment, the mood disorder is depression. In one embodiment, the mood disorder is dysthymia.

An aspect of the invention is in the treatment of stress-induced or stress-related mood disorder, e.g., dysthymia. An aspect of the invention is in the treatment of an anxiety disorder. In one embodiment, the anxiety disorder is selected from the group consisting of generalized anxiety disorder, panic disorder, panic disorder with agoraphobia, agoraphobia, social anxiety disorder, obsessive-compulsive disorder, and post-traumatic stress disorder. In one embodiment, the anxiety disorder is generalized anxiety disorder. In one embodiment, the anxiety disorder is post-traumatic stress disorder.

An aspect of the invention is in the treatment of stress-induced or stress-related anxiety.

An aspect of the invention is in enhancing muscle performance. In one embodiment, the muscle performance is selected from the group consisting of strength, speed, endurance and recovery. In humans, muscle function generally declines with age starting during the third decade of life; the decline generally accelerates after age 65. An aspect of the invention is thus in maintaining muscle performance during the aging process. The enhancement of muscle performance may be as part of the use of the compounds in sports nutrition, in aiding healthy aging (for example from age 45 to 65), and in slowing the rate of muscle decline in those aged over 65 (pre-frail)

An aspect of the invention is in the treatment of a muscle or neuromuscular disease. In one embodiment, the muscle or neuromuscular disease is a myopathy. In one embodiment, the muscle or neuromuscular disease is sarcopenia. In one embodiment, the muscle or neuromuscular disease is sporadic inclusion body myositis (sIBM). In one embodiment, the muscle or neuromuscular disease is a muscular dystrophy. In one embodiment, the muscle or neuromuscular disease is Duchenne muscular dystrophy.

An aspect of the invention is in the treatment of mitochondrial disease. For example, a subject may require treatment of poor growth, loss of muscle coordination, muscle weakness, visual problems, hearing problems, heart disease, liver disease, kidney disease, gastrointestinal disorders, respiratory disorders, neurological problems, autonomic dysfunction sometimes learning disabilities, and dementia as a result of mitochondrial disease.

Further diseases related to mitochondrial dysfunction include:

Diabetes mellitus and deafness (DAD); Leber's hereditary optic neuropathy (LHON); Leigh syndrome (subacute sclerosing encephalopathy); neuropathy, ataxia, retinitis pigmentosa, and ptosis (NARP); myoneurogenic gastrointestinal encephalopathy (MNGIE); Myoclonic Epilepsy with Ragged Red Fibers (MERRF); Mitochondrial myopathy, encephalomyopathy, lactic acidosis, stroke-like symptoms (MELAS); and mtDNA depletion.

Amongst cancers, there can specifically be mentioned solid tumours, for example prostate cancer, pancreatic cancer and colon cancer.

Dosing of Compounds of the Invention

The optimal dosage will depend upon the intended use of the formulation, and upon the individual subject. Dosing may for example be daily to weekly. In one embodiment, dosing is at least weekly. For example, a subject may receive one dose once weekly, twice weekly, thrice weekly, or every other day. In one embodiment, dosing is at least daily. For example, a subject may receive one or more doses daily. It is believed that dosing for greatest efficacy in humans involves extended, daily administration. Where extended use is contemplated, this may include use for 1 week, 2 weeks, 3 weeks, 1 month, 2 months, 3 months, 4 months, 5 months, 6 months, or even longer.

The formulations can be administered to human subjects in therapeutically effective amounts. Typical dose ranges are from about 0.01 microgram/kg to about 15 mg/kg of body weight per day. The dosage of drug to be administered is likely to depend on such variables as the type and extent of the disorder, the overall health status of the particular subject, the specific compound being administered, the excipients used to formulate the compound, and its route of administration. Routine experiments may be used to optimize the dose and dosing frequency for any particular compound.

In one embodiment, the compound is administered at a concentration in the range from about 0.001 microgram/kg to greater than about 500 mg/kg. For example, the concentration may be 0.001, 0.01, 0.05, 0.1, 0.5, 1, 10, 50, 100 or 500 microgram/kg, or 1, 5, 10, 15, 20, 25, 30, 35, 40, 45, 50, 60, 70, 80, 90, 100, 150, 200, 250, 300, 350.0 mg/kg, 400 or 450.0 mg/kg, to greater than about 500 mg/kg or any incremental value thereof. It is to be understood that all values and ranges between these values and ranges are meant to be encompassed by the present invention.

In one embodiment, the compound is administered at a dosage in the range from about 0.2 milligram/kg/day to greater than about 100 mg/kg/day. For example, the dosage may be 0.2 to 100, 0.2 to 50, 0.2 to 25, 0.2 to 10, 0.2 to 7.5, 0.2 to 5, 0.25 to 100, 0.25 to, 0.25 to 25, 0.25 to 10, 0.25 to 7.5, 0.25 to 5, 0.5 to 50, 0.5 to 25, 0.5 to 20, 0.5 to 15, 0.5 to 10, 0.5 to 7.5, 0.5 to 5, 0.75 to 50, 0.75 to 25, 0.75 to 20, 0.75 to 15, 0.75 to 10, 0.75 to 7.5, 0.75 to 5, 1.0 to 50, 1 to 25, 1 to 20, 1 to 15, 1 to 10, 1 to 7.5, 1 to 5, 2 to 50, 2 to 25, 2 to 20, 2 to 15, 2 to 10, 2 to 7.5, or 2 to 5, mg/kg/day.

In one embodiment, the compound is administered at a dosage in the range from about 0.25 milligram/kg/day to about 50 mg/kg/day. For example, the dosage may be 0.25, 0.5, 0.75, 1.0, 1.25, 1.5, 1.75, 2.0, 2., 2.5, 2.75, 3.0, 3.25, 3.5, 3.75, 4.0, 4.25, 4.5, 4.75, 5, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, mg/kg/day.

For a typical human with a body weight in the range 60 to 90 kg, these dosages correspond to from 1.2 mg to 9 g/day. Examples of doses include from 10 mg to 5 g/day, for example from 50 mg to 2.5 g/day, for example from 100 mg to 2.0 g/day, for example from 100 mg to 1.5 g/day, for example from 100 mg to 500 mg per day, for example from 200 mg to 1.0 g per day.

In another embodiment, the compound is administered in concentrations that range from 0.01 micromolar to greater than or equal to 500 micromolar. For example, the dose may be 0.01, 0.02, 0.05, 0.1, 0.15, 0.2, 0.5, 0.7, 1, 3, 5, 7, 10, 15, 20, 25, 30, 35, 40, 45, 50, 60, 70, 80, 90, 100, 150, 200, 250, 300, 350, 400 or 450 micromolar, to greater than about 500 micromolar or any incremental value thereof. It is to be understood that all values and ranges between these values and ranges are meant to be encompassed by the present invention.

In yet another embodiment, the urolithin or precursor thereof is administered at concentrations that range from 0.1 microgram/mL to 500 microgram/mL. For example, the concentration may be 0.1, 0.5, 1, 2, 5, 10, 20, 25, 30, 35, 40, 45, 50, 60, 70, 80, 90, 100, 150, 200, 250, 300, 350, 400 or 450 microgram/mL, to greater than about 500 microgram/mL or any incremental value thereof. It is to be understood that all values and ranges between these values and ranges are meant to be encompassed by the present invention.

Preferred compounds of the invention have a solubility of over 0.5 mg/mL; more preferred compounds have a solubility of over 1.0 mg/mL; still more preferred compounds have a solubility of over 1.5 mg/mL. Accordingly, the doses mentioned above can be provided in a solution of from 5 ml to 6 L of solution. For some doses, especially any dose requiring the subject to take more than 1 L of solution, it is convenient to divide the daily dose into several fractions, to be taken at intervals through the day. For example, a subject may take from 10 ml to 1.5 L of solution as the daily dose, for example from 20 ml to 1 L, for example from 25 ml to 500 ml as the daily dose, for example from 50 ml to 350 ml, for example from 100 ml to 500 ml. A dose, which may be a daily dose, may for example be 20 ml, 40 ml, 50 ml, 100 ml, 200 ml, 250 ml, 300 ml to 400 ml or 500 ml.

Thus, for example, a solution of a compound of the invention at 1.5 mg/mL can be provided in a volume of 100 to 500 ml to provide a daily dose of 150 to 750 mg. A solution of a compound of the invention at 2.0 mg/mL can be provided in a volume of 50 to 500 ml to provide a daily dose of 100 to 1000 mg.

When the compound of the invention breaks down in the body of a subject to provide Urolithin, it provides a lower weight of urolithin to the subject than the weight of prodrug compound administered. The dose of urolithin that the subject receives can be calculated based on the molecular weight of the pro-drug compound of the invention and the molecular weight of the particular urolithin compound in question. If a particular dose of urolithin parent compound is desired, the dose of pro-drug that should be administered to achieve the dose can be calculated based on the molecular weight of the pro-drug compound of the invention and the molecular weight of the particular urolithin compound in question. For example, a dose of urolithin compound of from 100 mg to 1.5 g per day may be desired.

The effective amount of the compound will vary depending upon the manner of administration, the age, body weight, and general health of the subject. Factors such as the disease state, age, and weight of the subject may be important, and dosage regimens may be adjusted to provide the optimum response. A therapeutically effective amount of the compound may for example range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. Treatment may be by way of a single treatment or, preferably, can include a series of treatments. In one example, a subject is treated with the compound in the range of between about 0.1 to 20 mg/kg body weight, once per week for between about 1 to 10 weeks, preferably between 2 to 8 weeks, more preferably between about 3 to 7 weeks, and even more preferably for about 4, 5, or 6 weeks. It will also be appreciated that the effective dosage of the compound may increase or decrease over the course of a particular treatment.

The following Examples illustrate the invention.

A) Synthesis of Example Compounds

All urolithin-aminoacyl analogues were synthesised according to the general scheme below, where R is the relevant side chain, depending on the amino acid used.

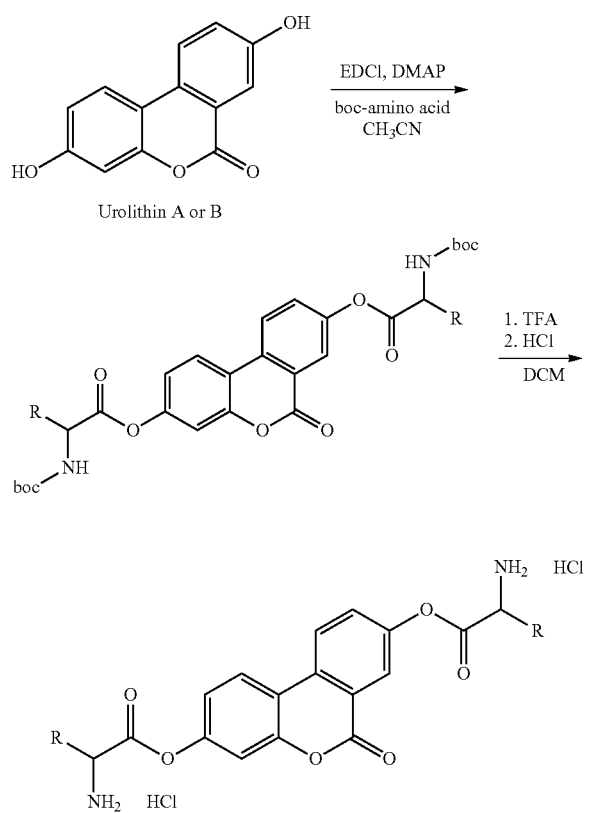

Example 1: Di-glycine-Urolithin A: 8-[(2-Aminoacetyl)oxy]-6-oxo-6H-benzo[c]chromen-3-yl 2-aminoacetate dihydrochloride

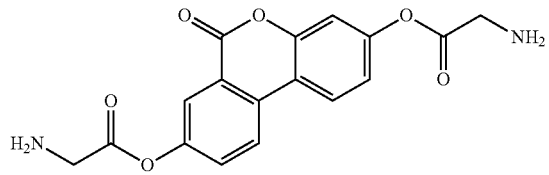 [SMILES: NCC(=O)Oc1ccc2c(c1)oc(=O)c1cc(OC(=O)CN)ccc12]

i) Preparation of the Intermediate Compound 8-[(2-{[(tert-Butoxy)carbonyl]amino}acetyl)oxy]-6-oxo-6H-benzo[c]chromen-3-yl 2-{[(tert-butoxy)carbonyl]amino}acetate Urolithin A (50 mg, 0.22 mmol) was dissolved in dry acetonitrile (4 mL), N-boc-glycine (81 mg, 0.46 mmol), DMAP (13 mg, 0.11 mmol) and EDCI (88 mg, 0.46 mmol) were added. The reaction mixture was stirred at room temperature overnight. The precipitate formed was collected by filtration and rinsed with water and dry acetonitrile to give the title compound as a white solid. Yield 35 mg (29%). LC purity 92%. MS m/z 431 [M+H]$^+$–(2×t-Bu).

ii) Preparation of the Final Product

8-[(2-{[(tert-butoxy)carbonyl]amino}acetyl)oxy]-6-oxo-6H-benzo[c]chromen-3-yl 2-{[(tert-butoxy)carbonyl]amino}acetate: (30 mg, 0.055 mmol) was suspended in dichloromethane (4 mL) and trifluoroacetic acid (450 uL) was added. The reaction mixture was stirred for 1 hour and concentrated. The residue was suspended in dichloromethane (4 mL) and concentrated. 1.25 M HCl in MeOH (4 mL) was added to the residue followed by 10 drops of water. The solution was concentrated and the white solid was suspended in 1.25 M HCl in MeOH (4 mL) and concentrated to give the title compound as a white solid. Yield 19 mg (83%). LC purity 95%. MS m/z 343 [M+H]$^+$.

Example 2: Di-alanine-Urolithin A: 8-{[(2R)-2-Aminopropanoyl]oxy}-6-oxo-6H-benzo[c]chromen-3-yl (2S)-2-aminopropanoate dihydrochloride

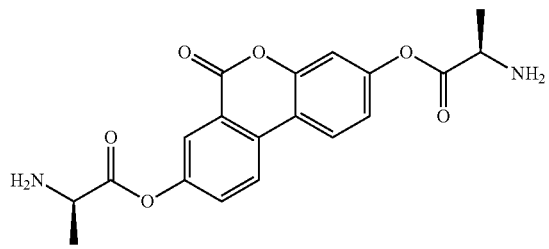 [SMILES: C[C@@H](N)C(=O)Oc1ccc2c(c1)oc(=O)c1cc(OC(=O)[C@@H](C)N)ccc12]

i) Preparation of the Intermediate Compound 8-{[(2R)-2-{[(tert-Butoxy)carbonyl]amino}propanoyl]oxy}-6-oxo-6H-benzo[c]chromen-3-yl (2S)-2-{[(tert-butoxy)carbonyl]amino}propanoate Urolithin A (50 mg, 0.22 mmol) was dissolved in dry acetonitrile (4 mL), N-boc-L-alanine (87 mg, 0.46 mmol), DMAP (13 mg, 0.11 mmol) and EDCI (88 mg, 0.46 mmol) were added. The reaction mixture was stirred at room temperature overnight and the precipitate was collected by filtration, rinsed with dry acetonitrile and dried in vacuo. Yield 48 mg (37%). LC purity 95%. MS m/z 459 [M+H]$^+$–(2×t-Bu).

ii) Preparation of Final Product

8-{[(2R)-2-{[(tert-Butoxy)carbonyl]amino}propanoyl]oxy}-6-oxo-6H-benzo[c]chromen-3-yl (2S)-2-{[(tert-butoxy)carbonyl]amino}propanoate (40 mg, 0.07 mmol) was dissolved in dichloromethane (3 mL) and trifluoroacetic acid (1 mL) was added. The reaction mixture was stirred for 4 hours and was then concentrated. The residue was suspended in 1.25 M HCl in MeOH (2 mL) and concentrated. The white solid was suspended in 1.25 M HCl in MeOH (2 mL) and concentrated to give the title compound. Yield 28 mg (90%). LC purity 95%. MS m/z 371 [M+H]$^+$.

Example 3: Glycine-Urolithin B:
6-Oxo-6H-benzo[c]chromen-3-yl 2-aminoacetate hydrochloride

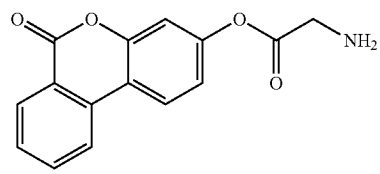 [SMILES: NCC(=O)Oc1ccc2c(c1)oc(=O)c1ccccc12]

i) Preparation of the Intermediate Compound 6-oxo-6H-benzo[c]chromen-3-yl 2-{[(tert-butoxy)carbonyl]amino}acetate Urolithin B (50 mg, 0.24 mmol) was dissolved in dry acetonitrile (4 mL), N-boc-glycine (45 mg, 0.26 mmol), DMAP (7 mg, 0.06 mmol) and EDCI (50 mg, 0.26 mmol) was added. The reaction mixture was stirred for 4 hours at room temperature. The precipitate formed was collected by filtration, rinsed with acetonitrile and dried in vacuo to give the title compound as a white solid. Yield 28 mg (32%). LC purity 100%. MS m/z 314 [M+H]$^+$–t-Bu.

ii) Preparation of Final Compound

6-Oxo-6H-benzo[c]chromen-3-yl 2-{[(tert-butoxy)carbonyl]amino}acetate (25 mg, 0.068 mmol) was dissolved in dichloromethane (3 mL) and trifluoroacetic acid (1 mL) was added. The reaction mixture was stirred for 1 hour and was then concentrated. The residue was suspended in 1.25 M HCl in MeOH (2 mL) and concentrated. To the residue was added 1.25 M HCl in MeOH (2 mL) and the solution was concentrated to give the title compound as a white solid. Yield 17 mg (82%). LC purity 95%. MS m/z 270 [M+H]$^+$.

Example 4: Di-leucine-Urolithin A: 8-{[(2R)-2-Amino-4-methylpentanoyl]oxy}-6-oxo-6H-benzo[c]chromen-3-yl (2S)-2-amino-4-methylpentanoate dihydrochloride

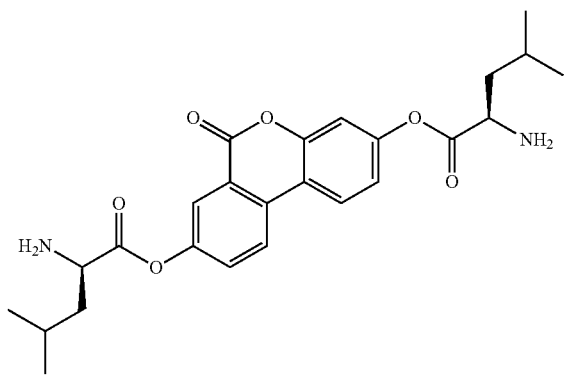 [SMILES: CC(C)C[C@@H](N)C(=O)Oc1ccc2c(c1)oc(=O)c1cc(OC(=O)[C@H](N)CC(C)C)ccc12]

i) Preparation of the Intermediate Compound 8-{[(2R)-2-{[(tert-Butoxy)carbonyl]amino}-4-methylpentanoyl]oxy}-6-oxo-6H-benzo[c]chromen-3-yl (2S)-2-{[(tert-butoxy) carbonyl]amino}-4-methylpentanoate Urolithin A (50 mg, 0.22 mmol) was dissolved in dry acetonitrile (4 mL), N-boc-L-leucine (106.4 mg, 0.46 mmol), DMAP (13 mg, 0.11 mmol) and EDCI (88 mg, 0.46 mmol) were added. The reaction mixture was stirred at room temperature for 2 hours. Dichloromethane (40 mL) was added and the mixture was washed with 0.1 M HCl (3×), water (2×) and dried (MgSO$_4$). The solution was concentrated to provide the title compound as a white solid. Yield 128 mg (88%). LC purity 95%. MS m/z 499 [M+H]$^+$–(2× t-Bu).

ii) Preparation of Final Product

8-{[(2R)-2-{[(tert-butoxy)carbonyl]amino}-4-methylpentanoyl]oxy}-6-oxo-6H-benzo[c]chromen-3-yl (2S)-2-{[(tert-butoxy)carbonyl]amino}-4-methylpentanoate (50 mg, 0.076 mmol) was dissolved in dichloromethane (3 mL) and trifluoroacetic acid (1 mL) was added. The reaction mixture was stirred for 2 hours and was then concentrated at 0° C. To the residue was added dichloromethane (1 mL) and 1.25 N HCl (0.5 mL). The solution was concentrated at 0° C. and the residue was dissolved in dichloromethane (1 mL) and 1.25 N HCl (0.5 mL) was added. The solution was concentrated and the white solid was suspended in dichloromethane (3 mL) and collected by filtration. Yield 20 mg (50%). LC purity 95%. MS m/z 455 [M+H]$^+$.

Example 5: Leucine-Urolithin B: 6-Oxo-6H-benzo[c]chromen-3-yl (2S)-2-amino-4-methylphentanoate hydrochloride

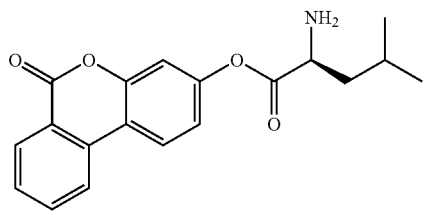 [SMILES: CC(C)C[C@H](N)C(=O)Oc1ccc2c(c1)oc(=O)c1ccccc12]

i) Preparation of the Intermediate Compound 6-oxo-6H-benzo[c]chromen-3-yl (2S)-2-{[(tert-butoxy)carbonyl]amino}-4-methylpentanoate Urolithin B (50 mg, 0.24 mmol) was dissolved in dry acetonitrile (4 mL), N-boc-L leucine (60 mg, 0.26 mmol), DMAP (7.1 mg, 0.06 mmol) and EDCI (50 mg, 0.26 mmol) were added. The reaction mixture was stirred at room temperature overnight. Water was added and the precipitate formed was collected by filtration and dried in vacuo to give a white solid. Yield 65.6 mg (64%). LC purity 97%. MS m/z 370 [M+H]$^+$–t-Bu.

ii) Preparation of the Final Product 6-oxo-6H-benzo[c]chromen-3-yl (2S)-2-{[(tert-butoxy)carbonyl]amino}-4-methylpentanoate (36 mg, 0.084 mmol) was dissolved in dichloromethane (3 mL) and trifluroacetic acid (0.5 mL) was added. The reaction mixture was stirred for 2 hours and was then concentrated at 0° C. The residue was dissolved in dichloromethane and concentrated followed by addition of 1.25 M HCl in MeOH (0.5 mL). The solution was concentrated, and the white solid was suspended in 1.25 M HCl in MeOH (1 mL) and concentrated to give the title compound. Yield 26 mg (77%). LC purity 95%. MS m/z 326 [M+H]$^+$.

Example 6: Proline-Urolithin B: 6-oxo-6H-benzo[c]chromen-3-yl (2S)-pyrrolidine-2-carboxylate hydrochloride

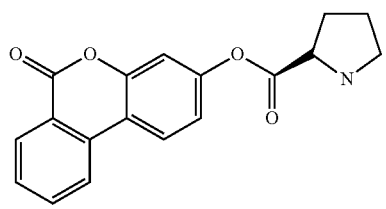

i) Preparation of the Intermediate Compound 1-tert-butyl 2-{6-oxo-6H-benzo[c]chromen-3-yl} (2S)-pyrrolidine-1,2-dicarboxylate Urolithin B (50 mg, 0.24 mmol) was dissolved in dry acetonitrile (4 mL), N-boc-L proline (56 mg, 0.26 mmol), DMAP (7.1 mg, 0.06 mmol) and EDCI (50 mg, 0.26 mmol) were added. The reaction mixture was stirred at room temperature overnight. Water was added and the precipitate was collected by filtration and dried in vacuo to give title compound as a white solid. Yield 57.5 mg (59%). LC purity 100%. MS m/z 354 [M+H]$^+$–t-Bu.

ii) Preparation of Final Product 1-tert-Butyl 2-{6-oxo-6H-benzo[c]chromen-3-yl} (2S)-pyrrolidine-1,2-dicarboxylate (41 mg, 0.10 mmol) was dissolved in dichloromethane (3 mL) and trifluoroacetic acid (0.5 mL) was added. The reaction mixture was stirred for 2 hours and concentrated. Dichloromethane was added to the residue and the solution was concentrated. The semisolid obtained was dissolved in dichloromethane (1 mL) and 1.25 M HCl in MeOH (0.5 mL) was added. The solution was concentrated and the residue was suspended in dichloromethane (1 mL) and 1.25 M HCl in MeOH (0.5 mL) was added. The solution was concentrated to give the title compound as a white solid. Yield 26 mg (75%). LC purity 95%. MS m/z 310 [M+H]$^+$.

HPLC Analysis

All HPLC analyses were carried out on a 5 μL sample on an Agilent 1100 series HPLC system including HPLC pump, auto injector, column oven and PDA detector with a Waters XBridgeC18, 50×2.1 mm, 5 μm column at a temperature of 40° C. and a flow rate of 0.4 mL/min using the following gradient:

Mobile phase A: 10 mM ammonium formate at pH 4
Mobile phase B: acetonitrile
0-0.25 min: 5% B
0.25-5 min: From 5% to 100% B
5-6 min: 100% B
6-6.1 min: From 100% to 5% B
6.1-8 min: 5% B UV detection took place at 215-395 nm, and a summary response of the full wavelength range was used when calculating the areas under the chromatogram peaks.

B) Solubility Experiments

A maximum amount of each compound was dissolved in 400 μL of phosphate buffer at pH 4 at room temperature in a filter vial (Agilent 0.45 μm PP Mini-UniPrep™). The filtered solutions were analysed by HPLC as described above. The peak area of the substance dissolved in buffer was compared to that of a standard prepared in DMSO. The solubilities for the tested compounds are given in Tables 6 and 7.

TABLE 6

Solubility of Urolithin A Compounds

| Urolithin A Compound | Solubility (mg/mL) | Molecular Mass | Solubility (mM/L) |
|---|---|---|---|
| Urolithin A | 0.00013 | 228.2 | 0.0057 |
| Example 1 (Di-glycine - UA) | 1.93 | 342 | 5.64 |
| Example 2 (Di-Alanine - UA) | 1.8 | 370 | 4.86 |
| Example 4 (Di-Leucine - UA) | 2.15 | 454 | 4.73 |

TABLE 7

Solubility of Urolithin B Compounds

| Urolithin B Compound | Solubility (mg/mL) | Molecular Mass | Solubility (mM/L) |
|---|---|---|---|
| Urolithin B | 0.00027 | 212.2 | 0.00127 |
| Example 3 (Glycine - UB) | 1.33 | 269 | 4.94 |

In all cases, the substituted urolithin compounds have a solubility at least $10^3$ times that of the parent urolithin compound (when considered on a mass or molar basis). The Di-glycine urolithin A compound (Example 1) is more soluble than the Glycine urolithin B compound (Example 3), possibly due to the presence of an additional solubilising aminoacyl group. Example 4, Di-leucine urolithin A, is particularly soluble compared to the parent compound.

C) Stability Experiments

The stability of the compounds in aqueous solution at room temperature was measured by dissolving the compounds in phosphate buffer of a pH chosen from 2, 3, 4, and/or 5. The compounds with low water solubility were first dissolved in DMSO and then diluted with phosphate buffer to contain 10% of DMSO. The samples were analysed by HPLC, as described above, at time 0 and several times thereafter. The peak area of the samples at these times were compared to the areas at t=0 to calculate the percentage remaining of the starting compound.

Figure 2:
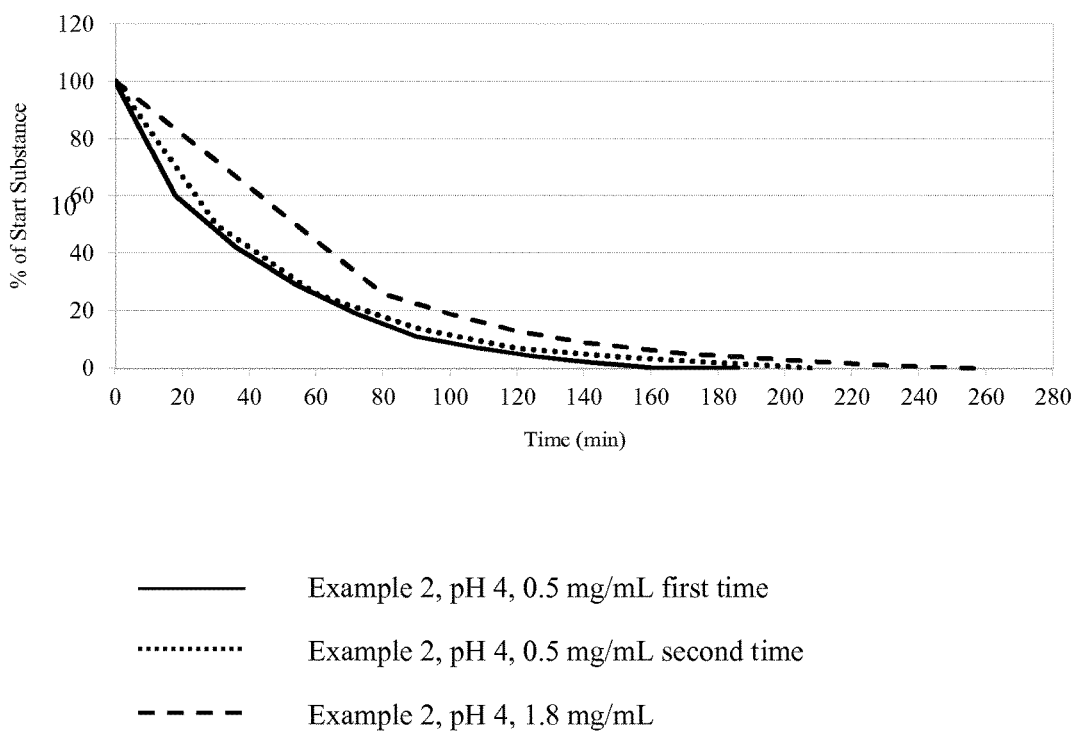
FIG. 2 shows the stability of the compound of Example 2 in solution over time.
Figure 3:
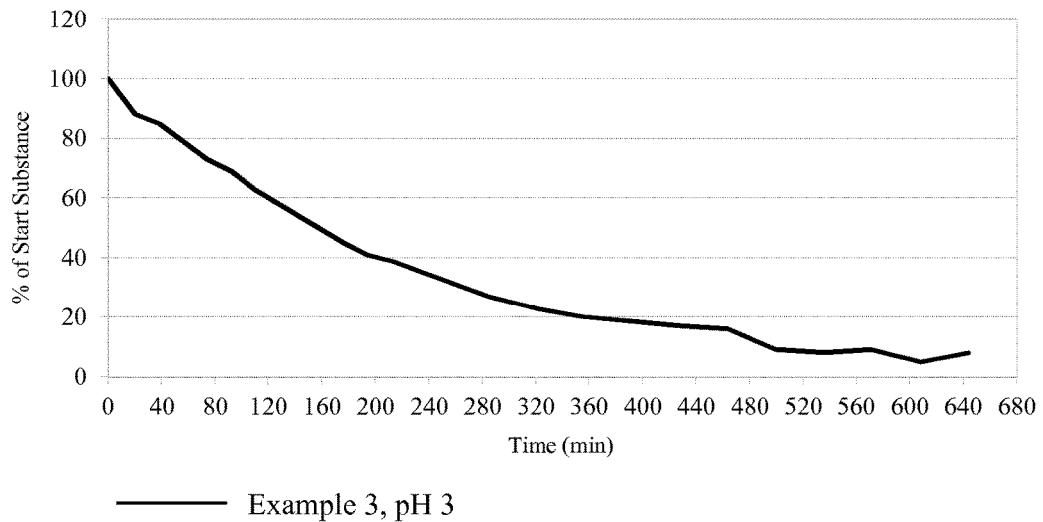
FIG. 3 shows the stability of the compound of Example 3 in solution over time.
Figure 4:
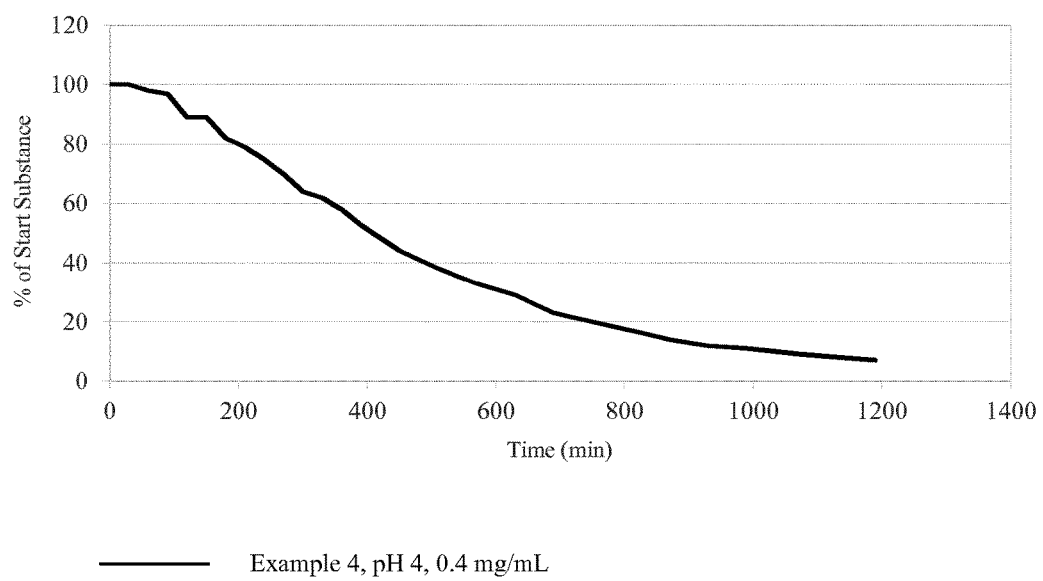
FIG. 4 shows the stability of the compound of Example 4 in solution over time.
Figure 5:
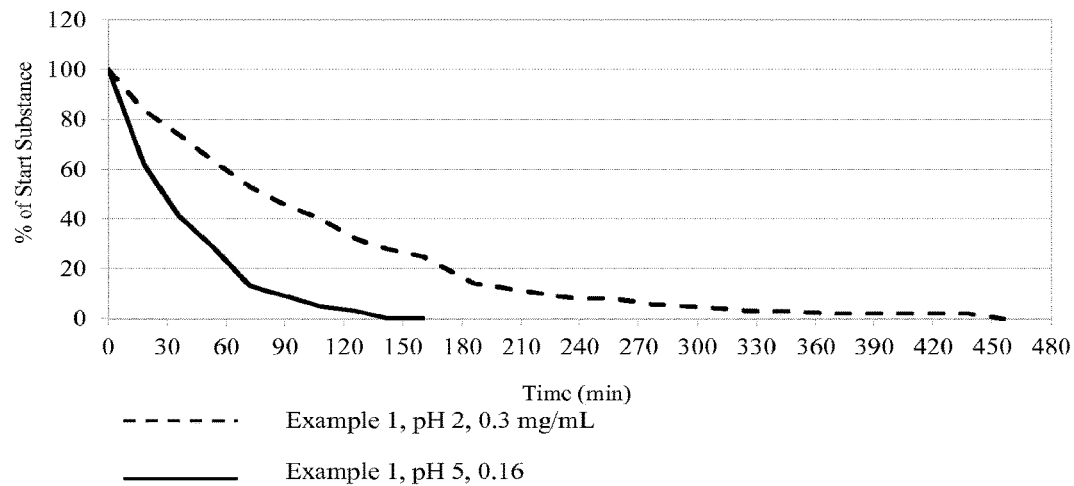
FIG. 5 shows the stability of the compound of Example 1 in solution over time at two different pHs.
Figure 6:
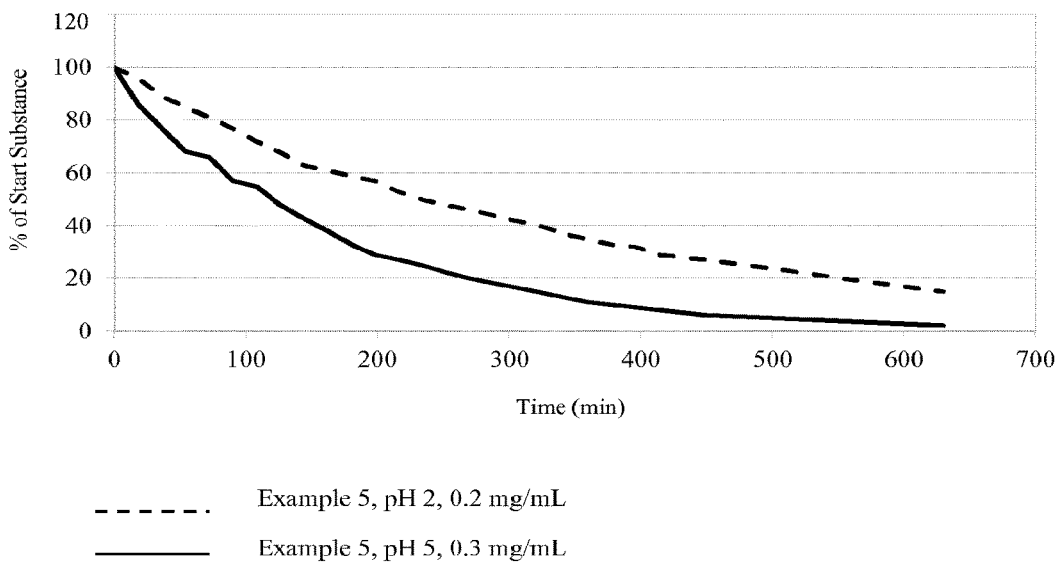
FIG. 6 shows the stability of the compound of Example 5 in solution over time at two different pHs.

The solutions were prepared for each of the compounds as set out in Table 8. Plots of the percentage remaining of starting substance over time for each of the compounds measured are given in FIGS. 1-6, and $t_{50}$ values (time taken for 50% of the starting compound to degrade) are given in Table 8.

TABLE 8

Degradation times for various compounds of the invention

| Figure | Compound | Solution | pH | $t_{50}$ (mins) |
|---|---|---|---|---|
| 1 | Example 1 Di-glycine - Urolithin A | 0.77 mg in 1 mL | 4 | 74 |
| 5 | Example 1: Di-glycine - Urolithin A | 0.16 mg in 1 mL | 2 | 81 |
| 5 | Example 1: Di-glycine - Urolithin A | 0.16 mg in 1 mL | 5 | 27 |
| 2 | Example 2: Di-alanine - Urolithin A (first time) | 0.94 mg in 1.8 mL | 4 | 29 |
| 2 | Example 2: Di-alanine - Urolithin A (second time) | 0.33 mg in 0.66 mL | 4 | 31 |
| 2 | Example 2: Di-alanine - Urolithin A | 0.72 mg in 0.4 mL | 4 | 56 |
| 3 | Example 3: Glycine - Urolithin B | 0.31 mg in 1 mL | 4 | 156 |
| 4 | Example 4: Di-leucine - Urolithin A | 0.4 mg in 1 mL | 4 | 405 |
| 6 | Example 5: Leucine - Urolithin B | 0.2 mg in 1 mL | 2 | 240 |
| 6 | Example 5: Leucine - Urolithin B | 0.3 mg in 1 mL | 5 | 125 |

Degradation is seen to occur more quickly in solution of a higher pH; an approximate two-fold increase in the rate of degradation of Example 5 takes place when the pH of the solution is increased from 2 to 5. At pH 4, Example 4 degrades more slowly than Example 3, which in turn degrades more slowly than Example 1, which in turn degrades more slowly than Example 2. At pH 2 and pH 5, Example 5 degrades more slowly than Example 1.

D) Oral Bioavailability Experiments

The oral bio availability of compounds of the invention can be assessed by orally administering a dose of compound in solution to Sprague-Dawley rats. Blood samples are collected from each rat before administration, and at intervals up to 24 hours thereafter. The blood samples are analysed for the plasma concentration of Urolithin. When Di-leucine-Urolithin A (Example 4) was given in a dose of 57.82 mg/kg in normal saline solution (0.9% NaCl), and in 15% DMSO, 85% water (containing 0.5% methylcellulose/ 0.25% Tween 80), it was found that Urolithin A was present at a mean concentration of 96.9 mg/ml at 15 minutes following administration in the case of the saline solution, and 42.67 mg/ml in the case of the DMSO/water solution. The Urolithin A was still present in the blood at a concentration of 2.6 mg/ml at 12 hours following administration in the case of the saline solution, and 1.30 mg/ml in the case of the DMSO/water solution. The C. and AUC of Urolithin A were higher when the compound of Example 4 was orally administered than when Urolithin A was orally administered. Surpisingly, this revealed that the soluble compound of Example 4 was able to deliver Urolithin A at least as effectively into the blood following oral administration as when Urolithin A was orally administered.

The experiment shows that the compounds of the invention are converted in the body into the parent urolithin compound. It further shows, surprisingly, that the compounds of the invention can be orally administered in different formulations and can still achieve similar levels of the urolithin compound in the blood.

CONCLUSIONS

All compounds of the invention tested show an enhanced solubility over the parent urolithins, and they degrade effectively into the parent urolithins over a $t_{1/2}$ timescale of from 27 to 405 minutes. This degradation occurs effectively when the compounds are administered orally, and the resulting parent urolithins are bioavailable. The compounds of the invention are particularly suitable for use as a medicament or a functional composition in solution.

Our copending patent application No. PCT/US2013/ 48310 (published as WO2014/004902) contains information useful for the proper understanding of the present invention, and the contents of its description are therefore incorporated herein in its entirety.

The invention claimed is:

1. A compound of formula (I) or a salt thereof: wherein:

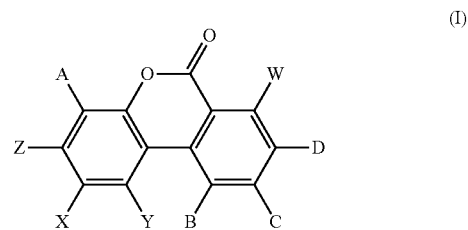

wherein:
A, B, and C are H,
D is selected from H and $OR^1$,
W, X and Y are each independently selected from H and $OR^1$,
Z is selected from H and $OR^1$;
provided that at least one of D, W, X, Y and Z is $OR^1$;
each $R^1$ is independently H or $C(=O)R^2$, and at least one $R^1$ group is $C(=O)R^2$;
each $R^2$ is selected from:
$CHR^3NHR^4$, where $R^4$ is H and $R^3$ is a group selected from $CH_3$, $CH_2CH(CH_3)_2$, $CH(CH_3)CH_2CH_3$, $CH_2Ph$, $CH_2$-3-(1H-indole), $CH_2CH_2SCH_3$, $CH_2OH$, $CHOHCH_3$, $CH_2SH$, $CH_2SeH$ and $CH_2PhpOH$, wherein said $R^3$ group can optionally be substituted by one or more groups selected from halogen, cyano, nitro, $OR^4$ or $C_1$-$C_4$ alkyl;

or $R^3$ and $R^4$ together with the C and N atoms to which they are attached form a 5-membered heteroalkyl ring, wherein said heteroalkyl ring can optionally be substituted by one or more groups selected from halogen, cyano, nitro, $OR^4$ or $C_1$-$C_3$ alkyl, wherein $R^4$ is $C_1$-$C_4$ alkyl optionally substituted with one or more halogen, cyano or nitro groups.

2. The compound of claim 1, wherein W is H, X is H, Y is H; and Z is $OR^1$.

3. The compound of claim 1, wherein $R^2$ is $CHR^3NHR^4$ where $R^4$ is H and $R^3$ is selected from $CH_3$, $CH_2CH(CH_3)_2$, $CH(CH_3)CH_2CH_3$, or $R^3$ and $R^4$ together with the C and N atoms to which they are attached form an unsubstituted 5-membered heteroalkyl ring.

4. The compound of claim 3, wherein the compound is selected from:

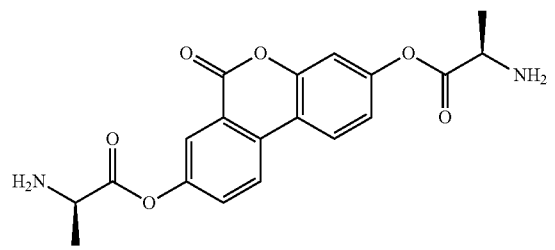

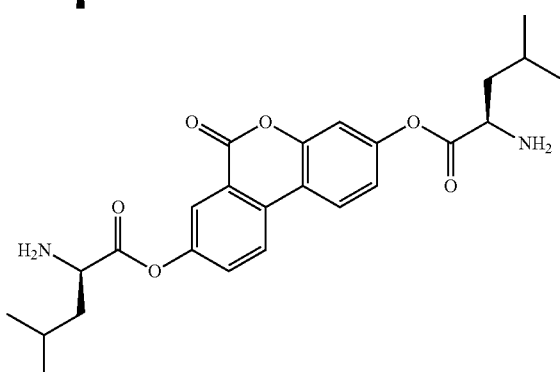

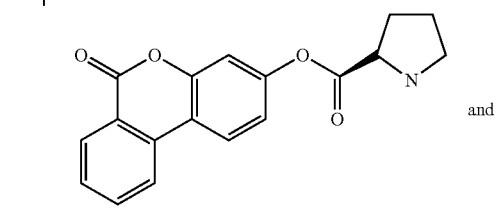

and

-continued

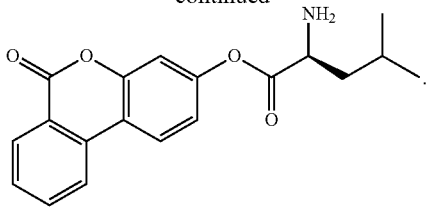

.

5. A pharmaceutical composition comprising at least one compound of claim 1; and a carrier.

6. The pharmaceutical composition of claim 5, wherein W, X and Y are H, and D and Z are both $OR^1$, and
each $R^1$ is independently H or $C(=O)R^2$, and at least one $R^1$ group is $C(=O)R^2$;
each $R^2$ is selected from:
$CHR^3NHR^4$ where $R^4$ is H and $R^3$ is selected from $CH_3$, $CH_2CH(CH_3)_2$, $CH(CH_3)CH_2CH_3$, $CH_2Ph$, $CH_2$-3-(1H-indole), $CH_2CH_2SCH_3$, $CH_2OH$, $CHOHCH_3$, $CH_2SH$, $CH_2SeH$ and $CH_2PhpOH$,
wherein said $R^3$ group can optionally be substituted by one or more groups selected from halogen, cyano, nitro, $OR^4$ or $C_1$-$C_4$ alkyl,
or $R^3$ and $R^4$ together with the C and N atoms to which they are attached form a 5-membered heteroalkyl ring, wherein said heteroalkyl ring can optionally be substituted by one or more groups selected from halogen, cyano, nitro, $OR^4$ or $C_1$-$C_3$ alkyl, wherein $R^4$ is $C_1$-$C_4$ alkyl, optionally substituted with one or more halogen, cyano or nitro groups.

7. The pharmaceutical composition of claim 5, wherein said pharmaceutical composition is in the form of a solution or suspension.

8. The pharmaceutical composition of claim 5, wherein said pharmaceutical composition is in the form of a powder or granules suitable for solution or suspension in an aqueous medium.

9. The pharmaceutical composition of claim 5, further comprising a further active ingredient selected from rapamycin, resveratrol, metformin, and spermidine.

10. The pharmaceutical composition of claim 5, wherein W is H, X is H, Y is H; and Z is $OR^1$.

11. A food, beverage or dietary supplement containing a compound of claim 1.

12. The food, beverage or dietary supplement of claim 11, which is in the form of a food additive, a food ingredient, a functional food, a medical food, a nutraceutical, a food supplement, a functional beverage, or a gel.

* * * * *